United States Patent [19]

Dorfman et al.

[11] Patent Number: 5,352,493
[45] Date of Patent: Oct. 4, 1994

[54] METHOD FOR FORMING DIAMOND-LIKE NANOCOMPOSITE OR DOPED-DIAMOND-LIKE NANOCOMPOSITE FILMS

[75] Inventors: Veniamin Dorfman, 8 Norman Dr., Shoreham, N.Y. 11786; Boris Pypkin, Moscow, U.S.S.R.

[73] Assignee: Veniamin Dorfman, Shoreham, N.Y.

[21] Appl. No.: 695,552

[22] Filed: May 3, 1991

[51] Int. Cl.$^5$ .............................................. B05D 3/06
[52] U.S. Cl. ................................... 427/530; 427/573; 427/574; 427/577; 427/578; 427/570; 427/249; 427/122; 427/62; 423/446; 428/408
[58] Field of Search ................. 427/38, 249, 122, 314, 427/62, 530, 577, 573, 574, 578, 570; 423/446; 428/408; 156/DIG. 68

[56] References Cited

U.S. PATENT DOCUMENTS

| | | |
|---|---|---|
| 4,191,735 | 3/1980 | Nelson et al. |
| 4,783,368 | 11/1988 | Yamamoto et al. |
| 4,816,291 | 3/1989 | Desphandey et al. |
| 4,822,466 | 4/1989 | Rabalais et al. |
| 4,842,937 | 6/1989 | Meyer et al. |
| 4,877,677 | 10/1989 | Hirocki et al. |
| 4,897,829 | 1/1990 | Ikoma et al. |
| 4,915,977 | 4/1990 | Okamoto et al. |
| 4,948,388 | 8/1990 | Ringwood |
| 4,960,643 | 10/1990 | Lemelson |
| 4,961,958 | 10/1990 | Desphandey et al. |
| 4,980,021 | 12/1990 | Kitamura et al. |
| 4,985,051 | 1/1991 | Ringwood |
| 4,992,298 | 2/1991 | Deutchman et al. |
| 5,002,899 | 3/1991 | Geis et al. |
| 5,040,501 | 8/1991 | Lemelson |
| 5,055,318 | 10/1991 | Deutchman et al. |
| 5,064,801 | 11/1991 | Juntgen et al. |
| 5,068,148 | 11/1991 | Nakahara et al. |
| 5,077,103 | 12/1991 | Wagner et al. |
| 5,087,434 | 2/1992 | Frenklach et al. |
| 5,094,915 | 3/1992 | Subramaniam |
| 5,100,424 | 3/1992 | Jang et al. |
| 5,101,288 | 3/1992 | Ohta et al. |
| 5,110,577 | 5/1992 | Tamor et al. |
| 5,135,808 | 8/1992 | Kimock et al. |
| 5,137,784 | 8/1992 | Suzuki et al. |
| 5,142,390 | 8/1992 | Ohta et al. |
| 5,169,579 | 12/1992 | Marcus et al. |
| 5,171,732 | 12/1992 | Hed |
| 5,174,983 | 12/1992 | Snail |
| 5,177,299 | 5/1992 | Kondo et al. |
| 5,183,602 | 2/1993 | Raj et al. |
| 5,190,807 | 3/1993 | Kimock et al. |
| 5,198,285 | 3/1993 | Arai et al. |
| 5,202,571 | 4/1993 | Hirabayashi et al. |
| 5,206,083 | 4/1993 | Raj et al. |
| 5,210,430 | 5/1993 | Taniguchi et al. |
| 5,219,769 | 6/1993 | Yonehara et al. |
| 5,243,199 | 9/1993 | Shiomi et al. |
| 5,256,483 | 10/1993 | Yamazaki et al. |

FOREIGN PATENT DOCUMENTS 2158086A  11/1985  United Kingdom.

OTHER PUBLICATIONS

Dorfman, "Diamond-like nanocomposites (DLN)", Thin Solid Films, 212 (1992) pp. 267–273.

*Primary Examiner*—Roy V. King
*Attorney, Agent, or Firm*—Nixon, Hargrave, Devans & Doyle

[57] ABSTRACT

The present invention relates to the formation of a class of nanocomposite amorphous materials consisting of interpenetrating random networks of predominantly sp3 bonded carbon stabilized by hydrogen, glass-like silicon stabilized by oxygen and random networks of elements from the 1–7b and 8 groups of the periodic table. The materials have high strength and microhardness, flexibility, low coefficient of friction and high thermal and chemical stability. Nanocomposites containing networks of metallic elements can have conductivity variable from insulating dielectric to metallic. The materials have a wide range of applications as protective coatings and as electrically active materials. Metallic nanocomposites can exhibit superconductivity at low temperatures.

11 Claims, 5 Drawing Sheets

METHOD FOR FORMING DIAMOND-LIKE NANOCOMPOSITE OR DOPED-DIAMOND-LIKE NANOCOMPOSITE FILMS

BACKGROUND OF THE INVENTION

1. Field of the invention

The invention relates to a new class of diamond-like solid state materials, especially films and coatings thereof, and methods of their manufacture. The materials include a clusterless diamond-like nanocomposite structure which contains interpenetrating networks of a diamond-like matrix stabilized by hydrogen, and a silicon glass-like network stabilized by oxygen, and contains, in addition to carbon, hydrogen, silicon and oxygen, and other elements, especially any or a combination of transition metals of 1b–7b, 8 groups of the periodic table.

2. Description of the prior art

Diamond-like carbon (dlc) films are unique materials which possess many of the technologically important properties of diamond, such as high hardness, high chemical stability, electrochemical and wear resistance, high electrical resistivity and high thermal conductivity. The amorphous nature of dlc films, unlike diamond, allows the synthesis of extremely uniform, smooth, nonporous, thin films with thicknesses as low as 10 nm and a low coefficient of friction. While the synthesis of diamond films require substrate temperatures in excess of about 800° C., dlc films can be synthesized at close to room temperature. Further, dlc films can be deposited on virtually any substrate material. As a result of these factors, a number of coating applications of dlc films have recently been developed.

Dlc films are formed by a variety of low pressure processes such as d.c., r.f. or microwave plasma decomposition of hydrocarbon gases, laser ablation of graphite and low energy carbon ion beam deposition.

A common factor in most of these processes is the bombardment of the growth surface by low energy ions in the range of about 100–1000 eV. However, there are serious problems related to the synthesis and application of dlc films. Key problems are low adherence to a number of useful substrates, high residual stress levels (particularly at the dlc/substrate interface) and a low fatigue threshold. Further, the high electrical resistivity of dlc films, limits their field of applications largely to protective coatings and some optical applications. A key problem is the low thermal stability of dle films. Complete graphitization occurs at temperatures above 600° C.

Recently, extensive work has been devoted to a new class of carbon-base micro-composites (R. d'Agostino, ed., *Plasma Deposition, Treatment, and Etching of Polymers*, Academic Press, San Diego, 1990). The term "composite" is used to stress that the main microstructural feature of this class of materials, distinguishable, for example, by electron microscopy, is the existence of regions of one of the constituents dispersed randomly in the matrix of another. At low concentration of metallic elements in an organic matrix, (dielectric regime) the microstructural inhomogeneities (small metallic inclusions) are randomly dispersed in the organic matrix. As the metal concentration is increased, the metal inclusions grow and form a maze network (transition regime). At the percolation threshold, which is characterized by macroscopic connectivity of the inclusions, most of the characteristics of the composite material change abruptly. By increasing the concentration of metal atoms further, a metallic regime is reached and the material can be characterized as a metallic continuum with dielectric inclusions. In this respect, plasma polymerized polymer/metal films differ fundamentally from plasma polymerized organometallic films, where the metals are usually dispersed as chemically bonded atoms.

A particular class of carbon-based microcomposites which have been investigated, are based on the inclusion of heavy metals, e.g. W, in an hydrogenated amorphous matrix. Usually, metals form carbides in such films. Weissmantel et al.(*J. Vac. Sci. Technol.* Vol. A 4, p. 2892, 1986.) fabricated amorphous carbon films containing extremely small metal clusters. However, upon annealing at temperatures above 1000K, a segregation of small carbide or small metal crystallites was observed. The presence of only a small amount of the metal ($\sim 3$ at %) appeared to influence the microstructure of the metastable carbon matrix, which exhibited a sharp drop in microhardness and resistivity.

SUMMARY OF THE INVENTION

According to an aspect of the invention, there is provided a new class of materials based on a diamond-like carbon (dle) matrix which serves as the host matrix for the synthesis of nanocomposite structures which includes an interpenetrating glass-like silicon network. The glass-like silicon network imparts high stability to the diamond-like carbon matrix. The high temperature stability of these nanocomposites exceeds that of crystalline diamond one while preserving the amorphous, diamond-like state.

Another feature of the invention is the introduction of transition metals into the dlc matrix during its growth, resulting in a composite structure of three semi-independent interpenetrating networks consisting of the dlc host network the silicon-oxygen network and the transition metal network. The electrical properties of this structure can be continuously varied over at least 18 orders of magnitude from a purely dielectric to a metallic state while preserving the basic properties of the dlc state. A transition to a superconducting state, with the absence of electrical resistivity, is observed at low temperatures for certain three-network nanocomposites. The presence of the silicon-based and the transition metal-based networks leads to a structural composite network, rather than compound formation with carbon or silicon. The two-network and three-network nanocomposite structures have unique mechanical, physico-chemical and electrical properties, and represent a fundamentally novel class of amorphous solid materials.

Another feature of the invention is the method of synthesis of the nanocomposite networks by co-deposition by dusterless beams of ions, atoms or radicals of the relevant elements, where the mean free path of each particle species exceeds the distance between its source and the growing film surface, and each beam contains particles of well defined energy. Carbon-containing particle beams can be produced by plasma discharge in a triode plasmatron and extracted as charged particles by a high-voltage field in a vacuum chamber and directed onto the substrate.

In a particular feature of the invention, organo-silicon compounds, e.g. siloxanes, are chosen as precursors for the C, H, Si, and O components. In this case, a specially designed system is required for introducing the precursor compound into the plasma generator. Metal containing particle beams can be produced by any, or by a combination, of known methods which prevents particle collisions in the deposition chamber.

Diamondlike nanocomposites have a wide range of applications ranging in areas such as protective coatings, electronic materials, superconducting current carrying films and wires, sensors, and biocompatible materials. The combination of the chemical and mechanical resistance of the diamond-like state, extreme temperature stability and wide range of electronic properties open the possibilities for a variety of applications.

BRIEF DESCRIPTION OF THE DRAWINGS

The main features of the invention will become apparent upon examination of the accompanying drawings wherein.

DETAILED DESCRIPTION OF THE INVENTION

Figure 1A:
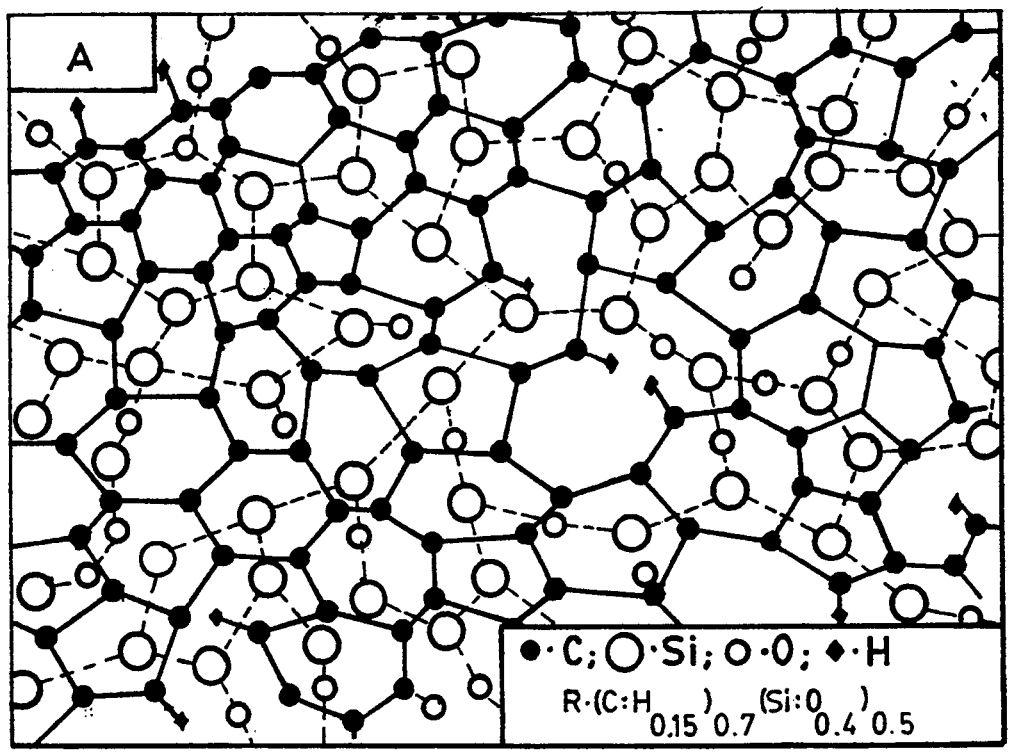
FIG. 1 is a schematic diagram showing the principle microstructure of two-network (A), intermediate (B), and three-network (C) nanocomposites.
Figure 1B:
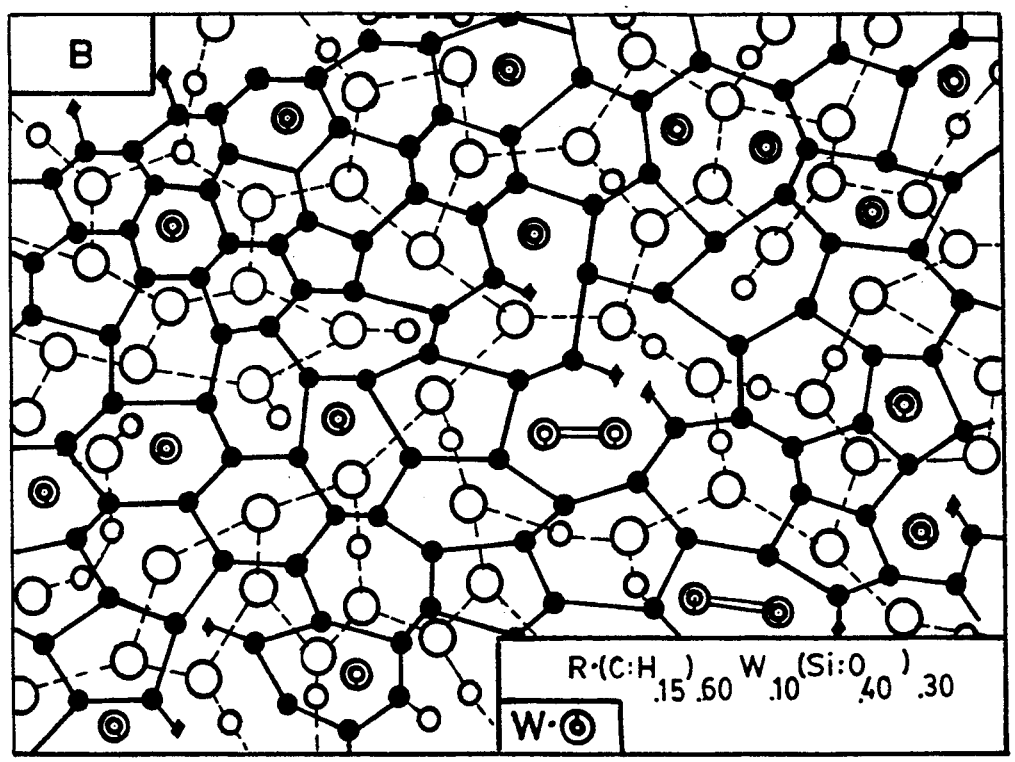

The microstructure of the new class of diamond-like nanocomposite solid state materials has a diamond-like carbon network stabilized by hydrogen, a glass-like silicon network stabilized by oxygen, with both networks mutually stabilizing each other as shown in FIG. 1(A). The materials may have a separate disordered network of alloying elements, as shown in FIG. 1 (B) and 1(C), especially any one or a combination of the transition metals of the groups 1b–7b and 8 of the periodic table, and all three networks (the carbon matrix, a-Si, and a-Me) are bonded to each other predominantly by weak chemical forces. The network elements other than carbon and hydrogen are hereafter referred to as alloying elements.

The carbon concentration in the diamond-like nanocomposites exceeds 40 atomic % of the sum of C and the other alloying elements. Hydrogen may or may not be present up to about 40 atomic % of the carbon concentration. The sum of the concentration of alloying elements exceeds 2 atomic %. The alloying elements include, but are not limited to, one or more of the following: B, Li, Na, Si, Ge, Te, O, Mo, W, Ta, Nb, Pd, Ir, Pt, V, Fe, Co, Mg, Mn, Ni, Ti, Zr, Cr, Re, Hf, Cu, Ag and Au.

The diamond-like nanocomposite materials have an amorphous structure and do not contain clusters or areas of ordering greater than 10 Angstroms. The alloying elements are distributed as separate atoms or as a separate disordered network, and all three networks (the carbon matrix, amorphous silicon, and amorphous metal) are bonded to each other predominantly by weak chemical forces.

The presence of the glass-like silicon network, stabilized by oxygen, serves to prevent the growth of graphitic carbon at high temperatures, to prevent metal cluster formation in metal-containing three-network nanocomposites, and reduce the internal stress in the nanocomposite structure and thereby enhance the adhesion to substrates.

The diamond-like nanocomposites have temperature stability far exceeding that of traditional diamond-like materials. Crystalline diamond is stable to approximately 1100° C., upon which graphitization occurs. Quartz has long term thermal stability to 1470° C., and short-time thermal stability up to 1700° C. The diamond-like nanocomposite structure has long term stability to 1250° C., and short term stability to 2000° C., i.e. its thermal stability exceeds that of crystalline diamond. In contrast, traditional, non-alloyed diamond-like films are stable only to about 600° C. before graphitization.

In the range from 600 to 1000 C. the chemical bonds of the carbon matrix of diamond-like nanocomposite materials partly change from sp3 to sp2. However, the general structure of the nanocomposite and their "diamond-like" properties are preserved. Under the same conditions, the usual diamond-like carbon is graphitized and losses its diamond-like properties.

Further, in the range from 400 to 500° C. (with 430 C. as the optimum), a reverse annealing is observed, whereby the ratio of sp3 to sp2 is increased.

The density of the C-Si two-network composites varies from 1.8 to 2.1 g/cm$^3$. The rest of the space is taken up by a random network of nanopores with diameter varying from 0.28 to 0.35 nm. The nanopore network does not form clusters and micropores. The alloying elements fill the nanopore network in a random fashion, resulting in a metal network without clusters or microcrystalline grains, even at concentrations as high as 50 atomic %. At densities below about 10 atomic % the alloying elements are distributed as separate atoms in the nanopores of the diamond-like matrix. The average distance between metal atoms in this quasi-random structure can be controlled by the density of the metal.

Figure 1C:
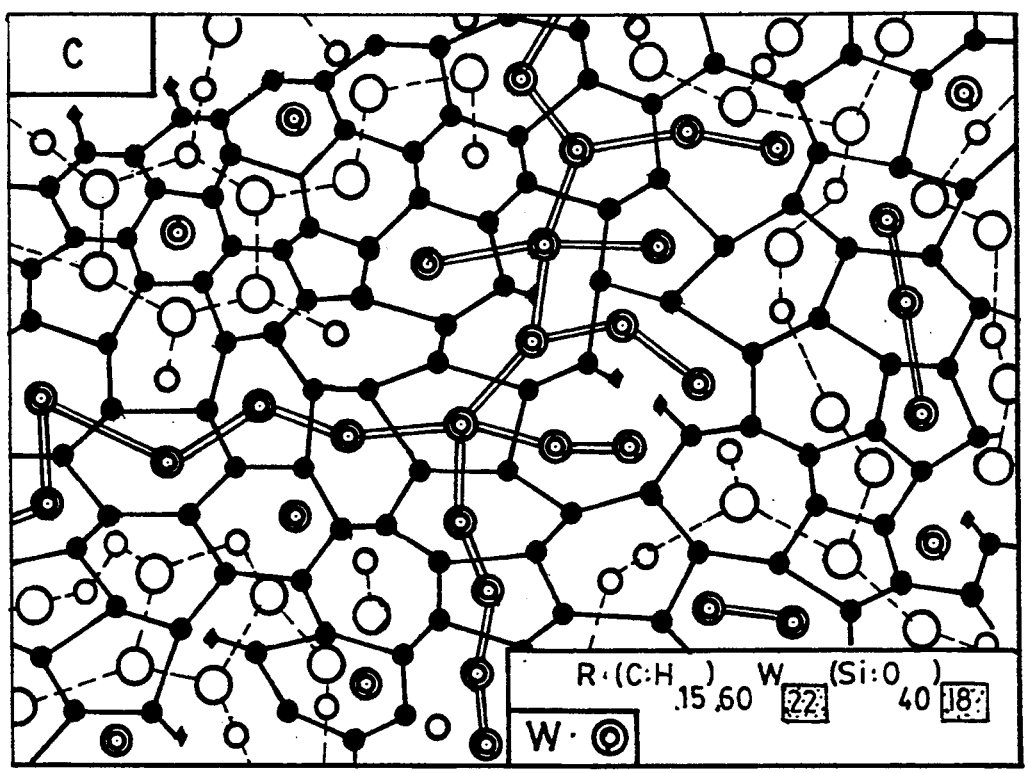
Figure 2:
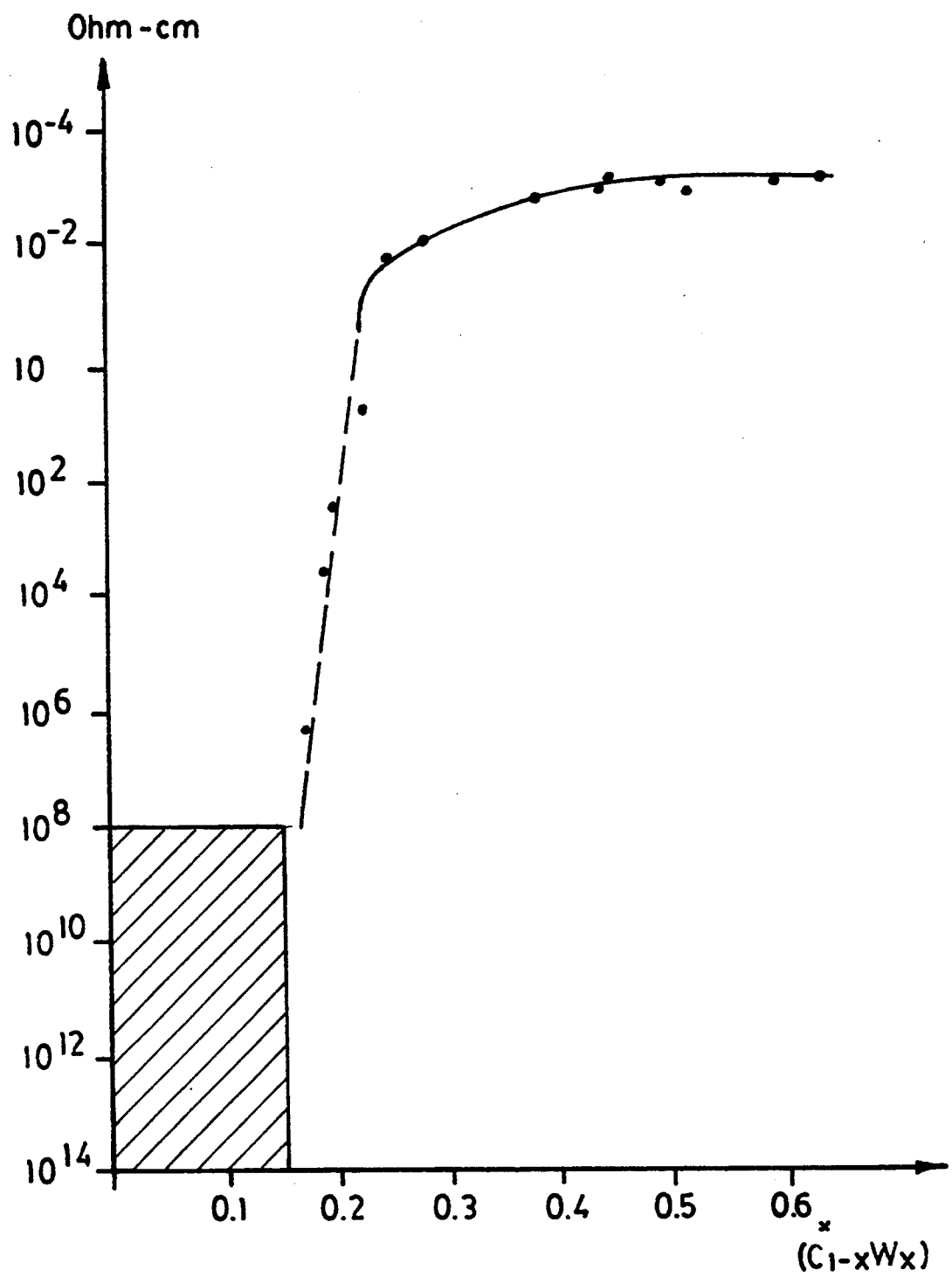
FIG. 2 is a schematic diagram showing the dependence of electrical resistivity on concentration for the case of a W-dlc nanocomposite.

When the density of the alloying metallic element reaches approximately 20–25 atomic %, the metals form a third, metallic, network in the nanocomposite structure, as shown in FIG. 1(C), resulting in a metal with diamond-like mechanical and chemical properties. FIG. 2 shows the resistivity in ohm-cm as a function of the concentration of W for a W-alloyed film. Metallic conductivity is reached for a W concentration in the range of 15–50 atomic % of the alloying element.

Figure 3:
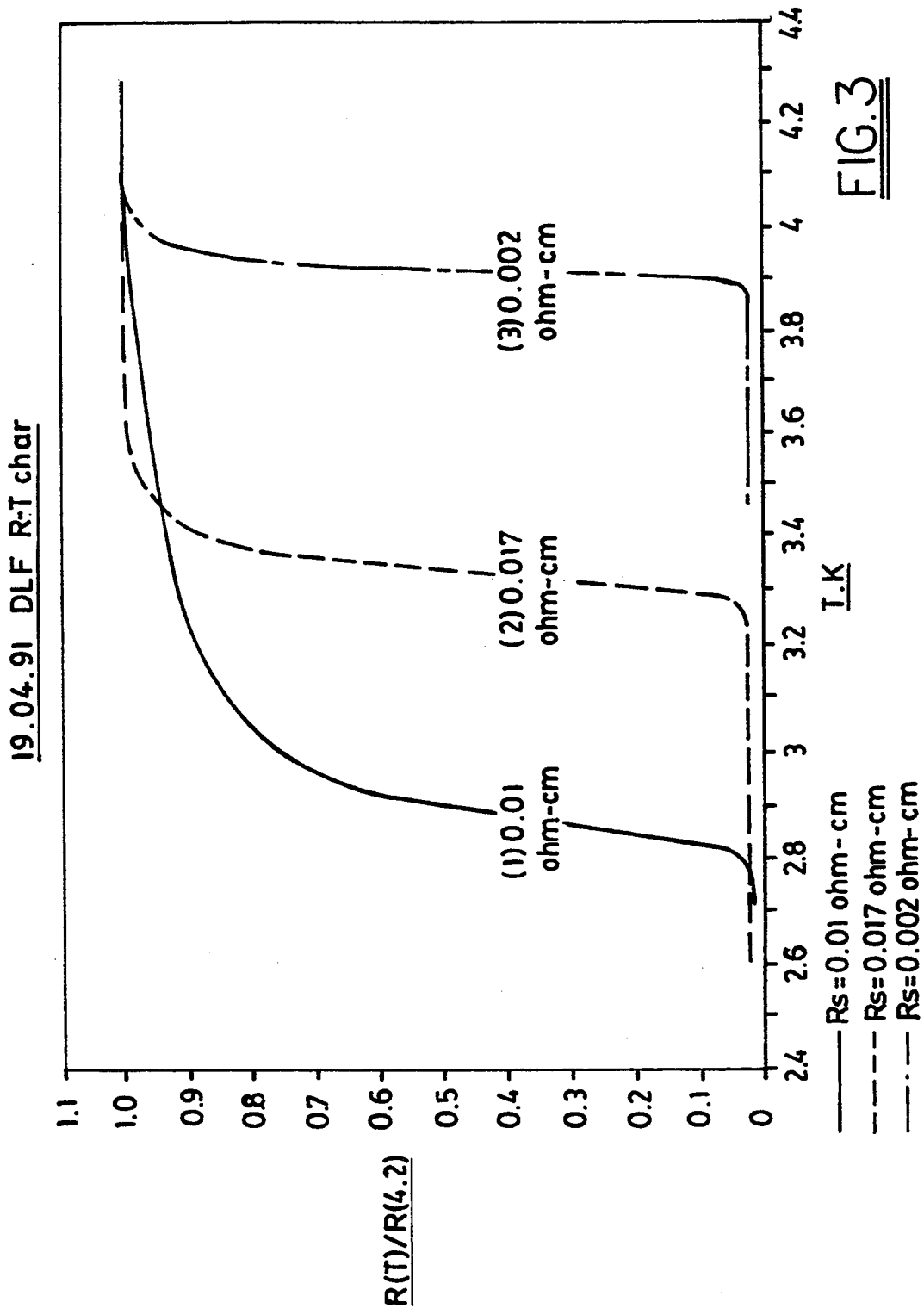
FIG. 3 is a schematic diagram showing the dependence of electrical resistivity on temperature for a W-alloyed film, demonstrating the transition to a superconducting state. Curves (1), (2) and (3) correspond to W-alloyed films with room temperature resistivities of 0.01, 0.017 and 0.02 ohm-cm, respectively.

At low temperatures the W-based three-network metallic nanocomposite undergoes a transition to a superconducting state with complete absence of electrical resistivity, as shown in FIG. 3, where the maximum superconducting transition temperature is 3.9K. The critical temperature for the transition to the superconducting state for the W-based nanocomposite is more than 300 times greater than the corresponding transition temperature for pure W metal. The transition temperature to a superconducting state depends on the concentration of the W alloying element. The number associated with each curve represents the room temperature resistivity of the material in units of ohm-cm. The three curves correspond to W concentration in the range of 15–50 atomic %.

In the intermediate concentration regime, with the density between about 10 atomic % and 20 atomic %, the metal atoms form a fragmented, random network, without macroscopic connectivity. The electronic properties of the fragmented metallic network depend strongly on external mechanical loading, pressure and electromagnetic fields. The diamond-like nanocomposites with alloying elements in this concentration regime have applications as smart materials and sensors.

The nanocomposites combine high microhardness with high elasticity. The microhardness ranges from 1500 to 3000 kg/mm$^2$ on the Vickers scale.

The key characteristics of the diamond-like nanocomposites is the absence of clusters on the atomic scale. Clusters destroy the local symmetry and serve as active centers of degradation.

The methods of fabrication have been developed to minimize the formation of dusters in the sources, in the primary plasma, in the deposition chamber and during the film growth. The materials can be synthesized by co-deposition of clusterless beams of ions, atoms and/or radicals, with the mean free path of each particle species exceeding the distance between its source and the growing film surface. At least 50% of the carbon-containing particles have kinetic energy above 100 eV, and the temperature of the substrate during growth should not exceed 500° C. The growth conditions for nanocomposite films are the following, referring to FIG. 4: the pressure in the deposition chamber 1 should not exceed $10^{-3}$ torr, the pressure in the active zone of plasma generation 2 is in the range $1.0 \times 10^{-3} - 5.0 \times 10^{-2}$ torr, the temperature of the substrate should not exceed 200° C., the temperature of the cathode filaments is in the range of 2100–2950° C., the current in the cathode filaments is 70–130 A, the voltage across the filament is 20–30 V, the voltage of the cathode with respect to ground is 70–130 V, the plasma current is from 1.0–20.0 A, The voltage of the substrate holder is 0.3–5.0 Kv, all the carbon-containing species have kinetic energy in the range from 100 to 1200 eV, the silicon-containing particles have energy in the range from 25 to 300 eV, and the metal beams consist of free atoms or monatomic ions, and the kinetic energy of the metal atoms/ions does not exceed 25 eV. With a precursor flow rate of 0.5–5.0 cc/hour, the growth rate is 0.1–2.0 micrometers/hour.

Figure 4:
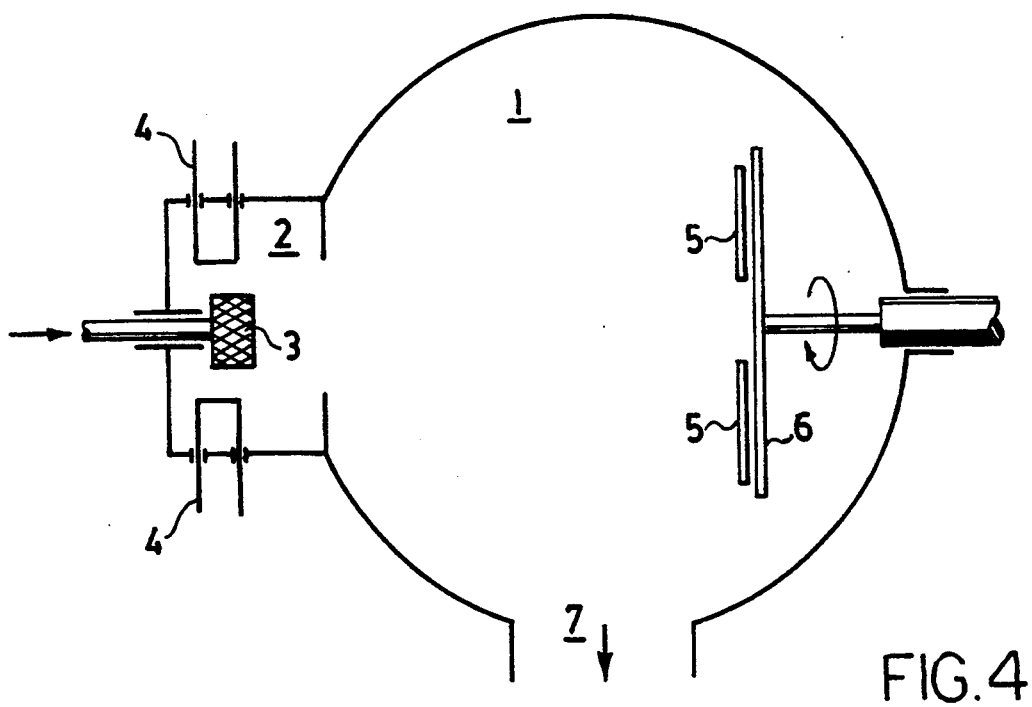
FIG. 4 is a schematic diagram detailing the main method of fabrication of the diamond-like nanocomposites. 1 is the vacuum deposition chamber, 2 is the plasma generation chamber, 3 is a porous ceramic for injection of liquid siloxane precursors, 4 are two resistively heated tungsten electrodes, 5 are substrates to be coated with diamond-like film, 6 is a substrate holder and 7 is a port connecting to a vacuum pump.

A preferred method of deposition uses a plasma discharge in a triode plasmatron, as shown schematically in FIG. 4, with the plasma energy density above 5 Kwh/gram-atom of carbon. The charge particles are extracted by a high-voltage field in the vacuum chamber and directed onto the substrate. It is preferable that the potential of the substrate holder is $-0.3$ to $+5.0$ Kv, and the most preferable $1.0 \pm 0.2$ Kv, and varying with a frequency in the range from 1 to 25 Mhz, and that the ratio of the electron emission to the carbon precursor flow in the plasmatron is from 0.5 to 1.5 electrons per particle.

Organosilicon compounds, such as siloxanes, are preferred precursors for C, H, Si, and O. One preferred organosilicon compound is polyphenylmethylsiloxane, containing from 1 to 10 silicon atoms. The high boiling point siloxanes may be introduced directly into the active plasma region through a microporous ceramic or metallo-ceramic (3 in FIG. 4 and FIG. 5) which is heated by thermocathodes (4). The photon and electron emission of the thermocathodes effect the evaporation, fragmentation and ionization of the precursor molecules on the surface of the ceramic, which thereby function as an ion source for the plasma generator. An alternative method for injection of the siloxane precursors is to use direct injection from a diffusion pump.

The formation of metal containing beams may be realized by any one of, or combination of the following methods: 1) by thermal evaporation; 2) by ion-sputtering; 3) by ion beams. The metal atom, or ion, beams are directed onto the growing film surface through the vacuum chamber to exclude interparticle collisions in the deposition chamber itself. Substrates are placed in an adjacent chamber on a multiposition drum which ensures double rotary motion, said adjacent chamber being connected to the plasma generation chamber by an opening for the emission of the atomic or ionic beams, as shown schematically in FIG. 4. A dc or a radio frequency potential is generally applied to the substrates during the deposition process. No external substrate heating is required.

Variation of the above described methods for deposition of diamond-like nanocomposite films include: the use of sputtered silicon and oxygen gas as precursors for Si and O; the use of sputtered solid $SiO_2$ as silicon and oxygen precursor; the use of sputtered carbon and hydrogen or hydrocarbon gas are used as carbon and hydrogen precursors; any combination of the above described methods.

Figure 5:
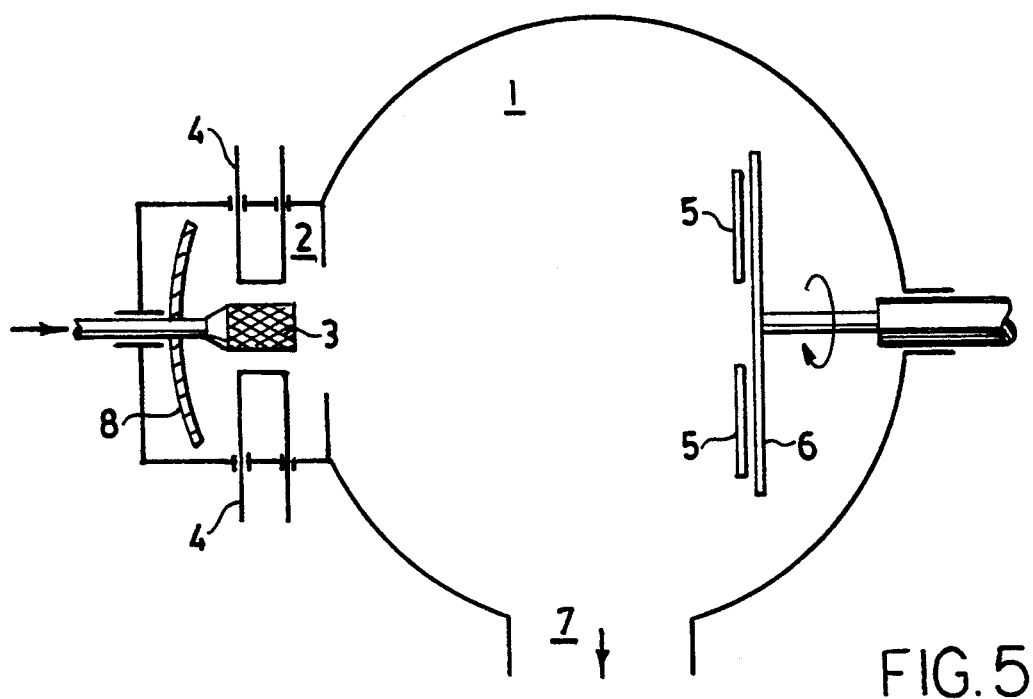
FIG. 5 is a schematic diagram detailing the methods of fabrication of diamond-like nanocomposites using reflected beam flow. 1 is the vacuum deposition chamber, 2 is the plasma generation chamber, 3 is a porous ceramic for injection of liquid siloxane precursors, 4 are two resistively heated tungsten electrodes, 5 are substrates to be coated with diamond-like film, 6 is a substrate holder, 7 is a port connecting to a vacuum pump and 8 is a reflecting electrode.

For deposition on non-conducting substrates, a method whereby a flow of neutral radicals is reflected from a high voltage target and directed to the substrate as shown schematically in FIG. 5.

The process employs depositions similar to those shown schematically in FIG. 4, except that a reflecting electrode 8 is used to generate a neutral beam. This process eliminates surface damage of the substrate resulting form charged and/or fast particles impinging on the substrate during film growth.

A preferred method for depositing ultra-thin dielectric diamond-like nanocomposite films consists of ion bombardment through (e.g. Ar+ or Kr+ with energy on the range 30–150 eV) through a vacuum chamber which has been backfilled by siloxane vapor (about $3 \times 104^{-4}$ torr). This results in a self-stabilized growth of a nanocomposite film, with the maximum thickness controlled by the maximum tunneling distance for the relaxation of the charge of the absorbed radicals. Extremely uniform and nonporous films with a thickness of 3–5 nm may thus be deposited. The maximum thickness is in the range of 6–8 nm.

The diamond-like nanocomposites have a wide range of applications ranging from protective coating against chemical wear and corrosion as well as applications as active materials for electronic applications. Stabilization of the structure of diamond-like films and the possibility to control the electrical conductivity by the creation of a third metallic network serves to enhance the range of applicability of this unique class of materials.

Some specific examples of applications of the diamond-like nanocomposite materials include the following:

EXAMPLE 1

Protective coatings for computer hard disks.

The combination of high microhardness with high elasticity and virtually absence of internal strain and stress provide strongly adhesive hard coatings for protection of computer hard disks and micromechanics devices. The coatings provide a stress-free interface and the strong adhesion to any magnetic layers of computer hard disk. The coatings are exceptionally smooth and have low coefficient of friction, providing self-lubrication effects to protect the recording head. Electrically conducting films provide anti-electrostatic protection, resulting in minimal dust coverage. Computer hard disks coated with diamond-like nanocomposite films with a thickness of 25–40 nm, were subjected to more than 30,000 start-stop cycles with no measurable change in the quality of the coating.

EXAMPLE 2

Schottky barriers

Three-network films containing heavy transition metals as W, can be used as Schottky barrier contacts for semiconductor device technology for high speed integrated circuits. Extremely stable, low leakage-current Schottky barrier contacts have been formed between three-network W-containing nanocomposite films and n-type Si and GaAs. The barrier heights and ideality factor were about 0.82–0.86 eV, 1.2–1.5 respectively, reverse breakdown voltages in excess of $-25V$ with GaAs and in excess of $-100$ V with Si. These values are comparable to those achieved for the best refractory metals, nitrides and silicides. In addition to forming Schottky barrier contacts, nanocomposite films can also serve as insulating, passivating and protecting films in Si and GaAs MIS structures, as optically transparent protective windows for GaAs optoelectronic circuits, and as gate material in serf-aligned FET technology.

EXAMPLE 3

Thermal resistors for ink-jet printheads

W-containing nanocomposites have been used as the thermal resistive elements in ink-jet printheads. The films exhibited higher stability than any material previously used. W-containing nanocomposite thermoresistors were subjected to more than $2 \times 10^8$ thermal cycles to temperatures above 1000° C. without change of the material properties.

EXAMPLE 4

Biocompatible protective coatings

Microbiological tests have shown complete chemical inertness of diamond-like nanocomposites to different cultures and tissues. Both plastic, metallic, and combined stomatological implants have been successfully protected by diamond-like nanocomposite coatings. In all cases which have been investigated, the undesirable side effects associated with implantation were dramatically reduced, particularly during the period of adaptation. The combination of hardness, flexibility, adhesion, low friction and biocompatibility provide excellent protective coatings to a variety of orthopedic devices and artificial implants as well as surgical tools.

EXAMPLE 5

Chemical protective coatings

Nanocomposite coatings have been demonstrated to be extremely stable protective coatings against highly reactive and corrosive organic and inorganic agents. For example, prolonged exposure, over the course of 9 months, to the highly corrosive aqueous environment at the bottom of the Black Sea, as well as exposure for 2 hours at 1523K in concentrated flowing HCl, has shown these films to be impermeable to these highly aggressive media. At the same time these coatings impart extreme smoothness and low coefficient of friction and minimizes the wear of the coated objects.

EXAMPLE 6

Electromechanical position sensors

Exceptionally stable and accurate electromechanical position sensors have been constructed based on nanocomposites with controlled resistivity. The sensors are based on a sliding metallic contact to an alloyed nanocomposite film with resistivity in the range of 0.1–10 ohm-cm, with 1.0 ohm-cm being the preferred resistivity. The thickness of the nanocomposite films is in the range of 0.01–1.0 micrometers, with the range 0.2–0.5 micrometers being the preferred range of thickness. A nanocomposite film with a resistivity of 1.0 ohm-cm and thickness of 0.5 micrometer provided a variance in the resistivity as a function of position of 0.02%.

EXAMPLE 7

Protective coatings optical devices

The unique combination of strong adhesion and protective properties against mechanical and chemical wear on the one hand, and high degree of transparency of two-network nanocomposites in a wide range of the ultraviolet, visible and infrared spectrum, has been taken advantage of in applications as protective coatings for mirrors, solar cells, infrared optical elements, sun glasses and glasses for arc welding. For example, germanium-based optical devices for high altitude aircrafts have been successfully protected by nanocomposite coatings with a thickness in the range of 300–3000 Angstroms; space-based solar cells were protected with coatings in the range of 300–2000 Angstroms; airport mirrors with diameter 800 mm were protected with coatings in the range of 300–2000 Angstroms; transmission of ultraviolet through sunglasses radiation was blocked with coatings in the range of 300–3000 Angstroms; and ultraviolet transmission through protective glasses for arc welding was blocked with coatings in the range of 2000–6000 Angstroms.

EXAMPLE 8

Antiallergenic protective coatings

The combination of biocompatibility, chemical and wear resistance, adhesion, barrier properties, low friction, and elasticity with controllable optical properties can provide antiallergic coatings for protection of jewelry, such as earrings, fabricated from saver and other metals. The allergic reaction to silver and other metals is widespread. Two-network coatings with a thickness of 0.03–1.0 micrometer were shown to block direct contact between the skin and the metallic allergen, resulting in the absence of any allergic reactions for silver earrings. In addition, the outward appearance of the jewelry can be preserved or new color created depending on the thickness, composition and growth conditions of the coatings. Two-layer or multilayer coatings can produce additional effects, such as having the outer layer provide antiallergic protection, and underlying layers provide different colored appearance, e.g. golden luster.

EXAMPLE 9

Decorative coatings

Two-network coatings are transparent and their refractive index can be varied from 1.9 to 2.5. The coatings can provide bright colored surfaces. With a thickness of the coatings below about 45 nm, the colors are uniform even on curved surfaces of metallic devices. Coatings with a thickness in the range of 1000-3000 Angstroms are multicolored on complex shapes. Coatings with thickness greater than 3000 Angstroms are uniformly dark colored. Golden and neutral colors (gray, dark-gray, deep dark blue and other) can be also be produced by depositing three-network coatings on metallic and nonmetallic surfaces.

EXAMPLE 10

Electron-transparent windows and coatings

Two-network nanocomposites with thickness 10-100 nm are transparent to electrons with energies in the range of 10-100 eV, while providing high barrier properties against air and vapor. These coatings have been used to stabilize the emission properties of multipoint cathodes. This allows the use of nanocomposite films as free-standing windows for vacuum electron devices.

EXAMPLE 11

Protective coatings for grids for color TV image tubes

Taking advantage of the combination of high thermal conductivity and low secondary emission, two-network nanocomposite films with a thickness in the range of 0.5-2.0 micrometers have been used as protective coatings on the grids of color TV image tubes. This resulted in enhanced image contrast and current parameters of the tube.

EXAMPLE 12

Superconducting nanocomposite films

The electrical conductivity of W-based nanocomposite films with thickness in the range of 2000 to 5,000 Angstroms and with a W concentration between 20 and 50 atomic % were measured at low temperatures using a helium cryostat. A transition to a superconductive state was observed at a temperature of 3.9K for a film which had a room temperature resistivity of 0.002 ohm-cm. The transition temperature is more than 300 times higher than that of pure tungsten metal. The films have applications as superconducting current carriers for transmission of electric power, as superconducting electrical interconnects on integrated circuits, and as superconducting contacts in Josephson junctions for the manufacture of superconducting quantum interference devices. Non-alloyed, dielectric diamond-like nanocomposite films can be used as the dielectric separator in the Josephson junctions.

What is claimed is:

1. A method of fabricating diamond-like nanocomposite or doped-diamond-like nanocomposite films containing the constituent elements carbon, hydrogen, silicon, oxygen and metal, comprising:

depositing onto a substrate by co-deposition a clusterless particle beams comprised of ions, atoms and/or radicals of said constituent elements, the free path length of each of particles of said constituent elements being in excess of the distance between its source and the growing film surface of the substrate; and wherein at least 50% of carbon particles comprise an energy above 100 eV, and the temperature of the substrate during growth is less than about 500° C.

2. The method of fabricating films according to claim 1, wherein the pressure during deposition does not exceed $3 \times 10^{-4}$ torr, the temperature of the substrate does not exceed 200° C. the carbon particles comprise an energy in the range from about 100 to 5,000 eV, silicon particles comprise an energy in the range of about 25 to 300 eV, and metal particles comprise free atoms or monatomic ions, the energy of the metal atoms/ions is less than about 25 eV.

3. The method of fabricating films according to claim 2, wherein the carbon particles are generated by a plasma discharge generator with a plasma energy density greater than 5 kWh/gram-atom, the carbon particles being extracted by a high-voltage field in vacuum and directed onto the substrate to be coated, the potential of the substrate being 0.3-5.0 kv varying with a frequency in the range from about 1 to 25 MHz, and the ratio of the electron emission rate to the carbon particles flow rate in the plasma discharge generator ranges from about 0.5 to 1.5 electrons per particle.

4. The method of fabricating films according to claim 3, wherein the constituent elements of carbon, hydrogen, silicon and oxygen are obtained from the decomposition of an organo-siloxane, and wherein the number of silicon atoms is from about 1 to 10.

5. The method of fabricating films according to claim 4, wherein the organo-siloxane is injected into the plasma discharge generator through a heated porous ceramic or metallo-ceramic.

6. The method of fabricating films according to claim 4, wherein the organo-siloxane is injected into the plasma discharge generator directly from a diffusion pump.

7. The method of fabricating films according to claim 4, wherein the carbon particles are created by sputtering a carbon target and the hydrogen particles are created using hydrogen as a hydrocarbon gas.

8. The method of fabricating films according to claim 4, wherein the silicon particles are created by sputtering a silicon target and the oxygen particles are created using an oxygen gas.

9. The method of fabricating films according to claim 1, wherein the particle beams are neutral radicals reflected from a high voltage target and directed onto the substrate to be coated.

10. The method of fabricating films according to claim 1, wherein the particle beams are generated by ion bombardment through a siloxane vapor introduced into a vacuum deposition chamber.

11. The method of fabricating films according to claim 3, wherein said organo-siloxane is polyphenylmethylsiloxane.

* * * * *